United States Patent
Evron et al.

(10) Patent No.: US 7,321,677 B2
(45) Date of Patent: Jan. 22, 2008

(54) SYSTEM AND METHOD FOR THREE-DIMENSIONAL RECONSTRUCTION OF AN ARTERY

(75) Inventors: Rami Evron, Tel Aviv (IL); Tsuriel Assis, Rehovot (IL); Ran Carmeli, Rinatia (IL)

(73) Assignee: Paieon Inc., New York, NY (US)

( * ) Notice: Subject to any disclaimer, the term of this patent is extended or adjusted under 35 U.S.C. 154(b) by 669 days.

(21) Appl. No.: 10/275,913

(22) PCT Filed: Mar. 2, 2001

(86) PCT No.: PCT/IL01/00201

§ 371 (c)(1),
(2), (4) Date: Nov. 12, 2002

(87) PCT Pub. No.: WO01/85030

PCT Pub. Date: Nov. 15, 2001

(65) Prior Publication Data

US 2003/0078500 A1    Apr. 24, 2003

Related U.S. Application Data

(63) Continuation of application No. 09/662,325, filed on Sep. 14, 2000, now abandoned.

(30) Foreign Application Priority Data

May 9, 2000    (IL) ..................................... 136050

(51) Int. Cl.
*G06K 9/00*     (2006.01)
*G06T 15/00*    (2006.01)

(52) U.S. Cl. ...................... 382/130; 382/154; 345/419; 128/922

(58) Field of Classification Search ...................... None
See application file for complete search history.

(56) References Cited

U.S. PATENT DOCUMENTS

| 5,175,773 | A | | 12/1992 | Garreau et al. |
| 5,734,384 | A | * | 3/1998 | Yanof et al. ................. 345/424 |
| 6,047,080 | A | | 4/2000 | Chen et al. |
| 6,501,848 | B1 | * | 12/2002 | Carroll et al. ............... 382/128 |

OTHER PUBLICATIONS

"Assessment of Diffuse Coronary Artery Disease by Quantitative Analysis of Coronary Morphology Based upon 3-D Reconstruction from Biplane Angiograms" by Wahle et al. Medical Imaging, IEEE Transactions on , vol. 14 Issue: 2, Jun. 1995 pp. 230-241.*

Garreau et al., "A Knowledge-Based Approach for 3-D Reconstruction and labeling of Vascular Networks from Biplane Angiographic Projections", *IEEE Transactions on Medical Imaging*, vol. 10, No. 2 (Jun. 1, 1991).

* cited by examiner

*Primary Examiner*—Bhavesh M Mehta
*Assistant Examiner*—Charles Kim
(74) *Attorney, Agent, or Firm*—Browdy and Neimark, PLLC

(57)    ABSTRACT

A method and system for imaging an artery contained in an arterial tree. A microprocessor generates a three-dimensional reconstruction of the arterial tree from two or more angiographic images obtained from different perspectives. The orientation of the axis of the artery in the arterial tree is then determined, and a perspective of the artery perpendicular to the axis of the artery is determined. A three dimensional reconstruction of the artery from angiographic images obtained from the determined perspective is then generated.

20 Claims, 3 Drawing Sheets

SYSTEM AND METHOD FOR THREE-DIMENSIONAL RECONSTRUCTION OF AN ARTERY

FIELD OF THE INVENTION

The present invention relates to medical devices, and more specifically to such devices for use in angiography.

BACKGROUND OF THE INVENTION

Stenosis of an artery refers to narrowing of the artery lumen due to plaque formation on the interior wall of the artery. The severity of the stenosis is the fraction of the cross-sectional area of the lumen that is occluded by plaque. Since narrowing is often asymmetrical about the axis of the artery, in order to assess the severity of a stenosis, it is necessary to obtain at least two, and preferably more, images perpendicular to the artery axis from orthogonal perspectives.

In angiography, the arterial lumen is filled with a radio-opaque substance and X-ray images of the arterial tree are obtained from different perspectives. Selection of these perspectives is partly arbitrary and partly a process of trial and error once a stenosis has been observed. However, the overall number of images that can be obtained is limited by time, safety and cost. Usually four to seven projections for the left coronary arterial system and two to four for the right coronary artery are obtained. The operator assesses the severity of the stenosis either on the basis of visual examination of the images or by computer analysis of a single image. Since these projections are in general not perpendicular to the arterial axis, estimation of stenosis severity and its length from these images is usually not accurate.

SUMMARY OF THE INVENTION

It is therefore an object of the invention to provide a more accurate process and system for computer reconstruction of an artery from discrete images of the artery.

Such an objective is realized in accordance with a first aspect of the invention by a system comprising means for obtaining two-dimensional angiographic images of arteries, and a microprocessor for processing the images. The images may be obtained, for example, by X-ray angiography or by ultrasound.

In accordance with a second aspect of the invention, there is provided a process for obtaining two or more angiographic images of an arterial tree. The images preferably include two images taken from perpendicular perspectives. In the case of the coronary arterial tree, all images are preferably obtained when the heart is in the same state, for example, diastole. A three dimensional (3D) reconstruction of the arterial tree is generated by the microprocessor from the images by methods known in the art. Methods of generating a 3D reconstruction of an arterial tree from discrete images can be found, for example, in anyone of the following references all of which are included herein in their entirety by reference: Faugeras, O. D., Mass. Inst. Tech. 1993; Garreau, et al., EEE Trans Med Imag 10(2):122-131; Grosskopf, S, Dissertation, Technical University of Berlin, 1994; and Hildebrand and Grosskopf, in Proc. Comp. Assisted Radiology CAR 95 conference, Berlin Springer, pp 201-207, 1995. The arterial tree may be, for example, the coronary arterial tree, the renal arterial tree, the pulmonary arterial tree, the cerebral arterial tree, or the hepatic arterial tree.

The 3D reconstructed arterial tree may be represented on a display screen using pseudo 3D effects such as directional lighting and shading. In a preferred embodiment, the reconstructed tree is presented as a stereoscopic pair of images to be viewed by the operator using a stereoscopic viewer. The reconstruction may be manipulated on the screen by the operator, allowing him, for example, to zoom in on a specific region or to rotate the reconstructed artery on the screen to obtain a desired perspective.

An artery, for example, a stenotic or aneurotic artery present in any of the obtained angiographic images may be detected by analysis of the images by the microprocessor or by visual examination of the images by the operator. The microprocessor determines the orientation of the axis of the artery in the 3D reconstruction of the arterial tree. The microprocessor then calculates two or more perspectives of the artery perpendicular to the arterial axis. Preferably, two orthogonal perspectives are determined. If images of the selected artery have not already been obtained approximately from the calculated perspectives, the operator obtains angiographic images of the artery from these perspectives and the microprocessor then constructs a 3D reconstruction of the artery from the angiographic images by methods known in the art. The invention thus allows an operator to obtain images of the artery from orthogonal perspectives more rapidly than is possible by prior art methods of trial and error. This allows a smaller radio-opaque dosage to the patient and a reduced exposure of the patient and the is operator to X-rays.

The microprocessor may apply metrological tools to the reconstructed artery. In the case of a stenotic artery, the microprocessor may provide accurate quantitative assessment of the extent and length of the stenosis. The severity of a stenosis may be described quantitatively, for example, by the fraction of the arterial lumen occupied by plaque.

The 3D reconstructed artery may be represented on a display screen using pseudo 3D effects such as directional lighting and shading. In a preferred embodiment, the reconstructed artery is presented as a stereoscopic pair of images to be viewed by the operator using a stereoscopic viewer. The reconstruction may be presented to the operator embedded in the 3D reconstruction of the entire arterial tree. The reconstruction may be manipulated on the screen by the operator, allowing him, for example, to zoom in on a specific region or to rotate the reconstructed artery on the screen to obtain a desired perspective of the stenosis including a perspective showing maximal narrowing or a cross section of the artery.

Thus, in its first aspect the invention provides a system for imaging an artery contained in an arterial tree, the artery having an axis, the system comprising:

a a microprocessor configured to aa generate a three-dimensional reconstruction of the arterial tree from two or more angiographic images of the arterial tree obtained from different perspectives;

ab determine an orientation of the axis of the artery in the arterial tree;

ac determine from the three-dimensional reconstruction of the arterial tree at least one perspective of the artery perpendicular to the axis of the artery; and ad generate a three dimensional reconstruction of the artery from angiographic images obtained essentially from the determined at least one perspective.

In its second aspect, the invention provides a method for imaging an artery contained in an arterial tree, the artery having an axis, the method comprising the steps of:

a generating a three-dimensional reconstruction of the arterial tree from two or more angiographic images of the arterial tree obtained from different perspectives;

b determining an orientation of the axis of the artery in the arterial tree;

c determining from the three-dimensional reconstruction of the arterial tree at least one perspective of the artery perpendicular to the axis of the artery; and d generating a three dimensional reconstruction of the artery from angiographic images obtained essentially from the determined at least one perspective.

In its third aspect, the invention provides a method for diagnosing stenosis in an arterial tree in an individual, the method comprising the steps of:

a generating a three-dimensional reconstruction of the arterial tree from two or more angiographic images of the arterial tree obtained from different perspectives;

b detecting in the three-dimensional reconstruction of the arterial tree a stenotic artery, the stenotic artery having an axis;

c determining an orientation of the axis of the stenotic artery;

d determining from the three-dimensional reconstruction of the arterial tree at least one perspective of the stenotic artery perpendicular to the axis of the artery;

e generating a three dimensional reconstruction of the artery from angiographic images obtained essentially from the determined at least one perspective; and f analyzing the three-dimensional reconstruction of the artery.

In its fourth aspect, the invention provides a program storage device readable by machine, tangibly embodying a program of instructions executable by the machine to perform method steps for imaging an artery contained in an arterial tree, the artery having an axis, said method steps comprising:

a generating a three-dimensional reconstruction of the arterial tree from two or more angiographic images of the arterial tree obtained from different perspectives;

b determining an orientation of the axis of the artery in the arterial tree;

c determining from the three-dimensional reconstruction of the arterial tree at least one perspective of the artery perpendicular to the axis of the artery; and d generating a three dimensional reconstruction of the artery from angiographic images obtained essentially from the determined at least one perspective.

In its fifth aspect, the invention provides a computer program product comprising a computer useable medium having computer readable program code embodied therein for imaging an artery contained in an arterial tree, the artery having an axis, the computer program product comprising a computer readable program code for causing the computer to generate a three-dimensional reconstruction of the arterial tree from two or more angiographic images of the arterial tree obtained from different perspectives;

b computer readable program code for causing the computer to determining an orientation of the axis of the artery in the arterial tree;

c computer readable program code for causing the computer to determine from the three-dimensional reconstruction of the arterial tree at least one perspective of the artery perpendicular to the axis of the artery; and d computer readable program code for causing the computer to generate a three dimensional reconstruction of the artery from angiographic images obtained essentially from the determined at least one perspective.

In its sixth aspect, the invention provides a program storage device readable by machine, tangibly embodying a program of instructions executable by the machine to perform method steps for diagnosing stenosis in an arterial tree in an individual, said method steps comprising:

a generating a three-dimensional reconstruction of the arterial tree from two or more angiographic images of the arterial tree obtained from different perspectives;

b detecting in the three-dimensional reconstruction of the arterial tree a stenotic artery, the stenotic artery having an axis;

c determining an orientation of the axis of the stenotic artery;

d determining from the three-dimensional reconstruction of the arterial tree at least one perspective of the stenotic artery perpendicular to the axis of the artery;

e generating a three dimensional reconstruction of the artery from angiographic images obtained essentially from the determined at least one perspective; and f analyzing the three-dimensional reconstruction of the artery.

In its seventh aspect, the invention provides a computer program product comprising a computer useable medium having computer readable program code embodied therein for diagnosing stenosis in an arterial tree in an individual the computer program product comprising:

a computer readable program code for causing the computer to generate a three-dimensional reconstruction of the arterial tree from two or more angiographic images of the arterial tree obtained from different perspectives;

b computer readable program code for causing the computer to detect in the three-dimensional reconstruction of the arterial tree a stenotic artery, the stenotic artery having an axis;

c computer readable program code for causing the computer to determine an orientation of the axis of the stenotic artery;

d computer readable program code for causing the computer to determe from the three-dimensional reconstruction of the arterial tree at least one perspective of the stenotic artery perpendicular to the axis of the artery;

e computer readable program code for causing the computer to generate a three dimensional reconstruction of the artery from angiographic images obtained essentially from the determined at least one perspective; and f computer readable program code for causing the computer to analyze the three-dimensional reconstruction of the artery.

BRIEF DESCRIPTION OF THE DRAWINGS

In order to understand the invention and to see how it may be carried out in practice, a preferred embodiment will now be described, by way of non-limiting example only, with reference to the accompanying drawings, in which.

DETAILED DESCRIPTION OF A PREFERRED EMBODIMENT

Figure 1:
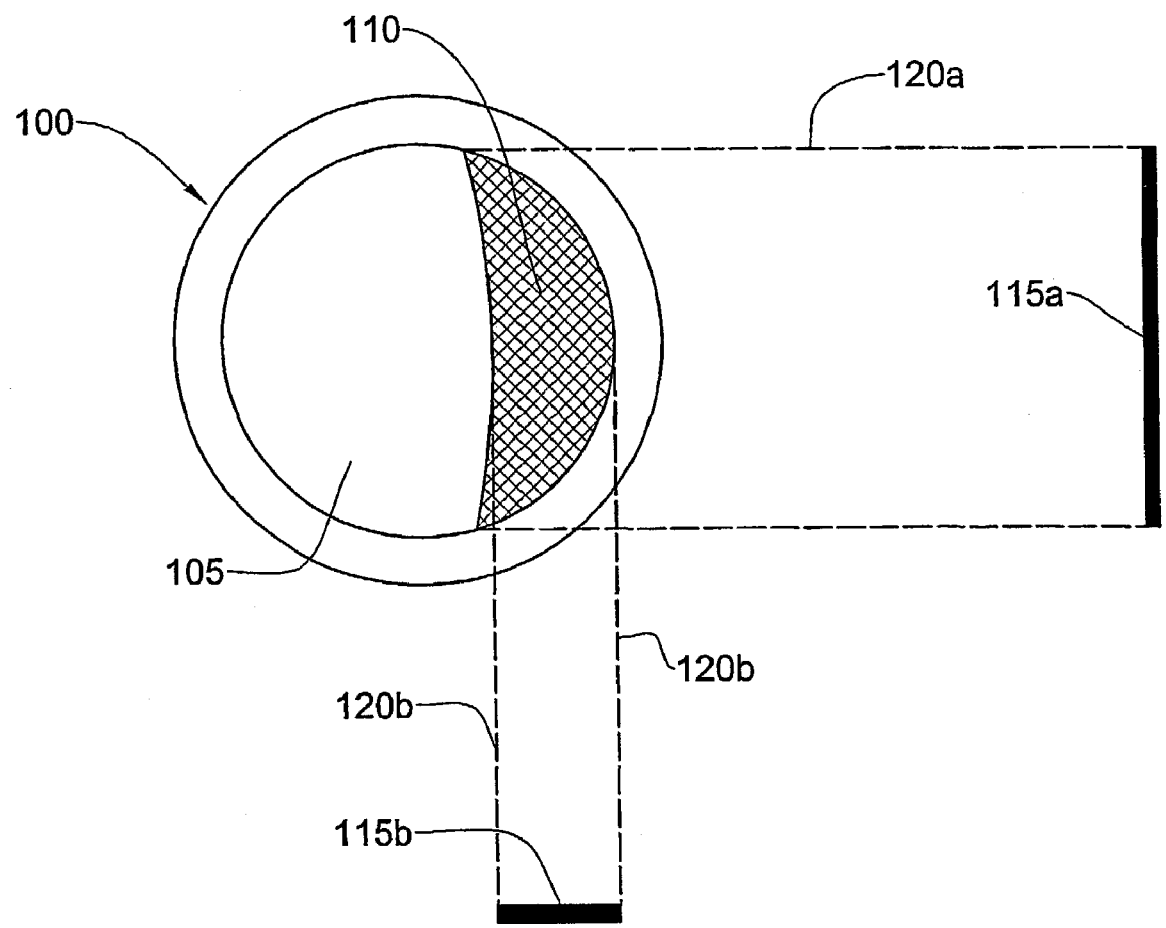
FIG. 1 shows a cross-sectional view and two projections of a stenotic artery.

Referring first to FIG. 1, a cross section 100 of a stenotic artery is shown. The artery has a circular lumen that is partially occluded by plaque 105. In angiography, the unoccluded portion of the lumen 110, (indicated in FIG. 1 by cross-hatching) is filled with a radio-opaque substance. 115a and 115b are two longitudinal projections of the radio-opacity of the artery as would be obtained in angiography. The projections 115a and 115b are from orthogonal perspectives as indicated by the broken lines 120a and 120b. In the projection 115a the stenosis appears to be non-critical. The projection 115b, on the other hand, shows maximal narrowing of the arterial lumen indicating that the stenosis is in fact critical.

Figure 2:
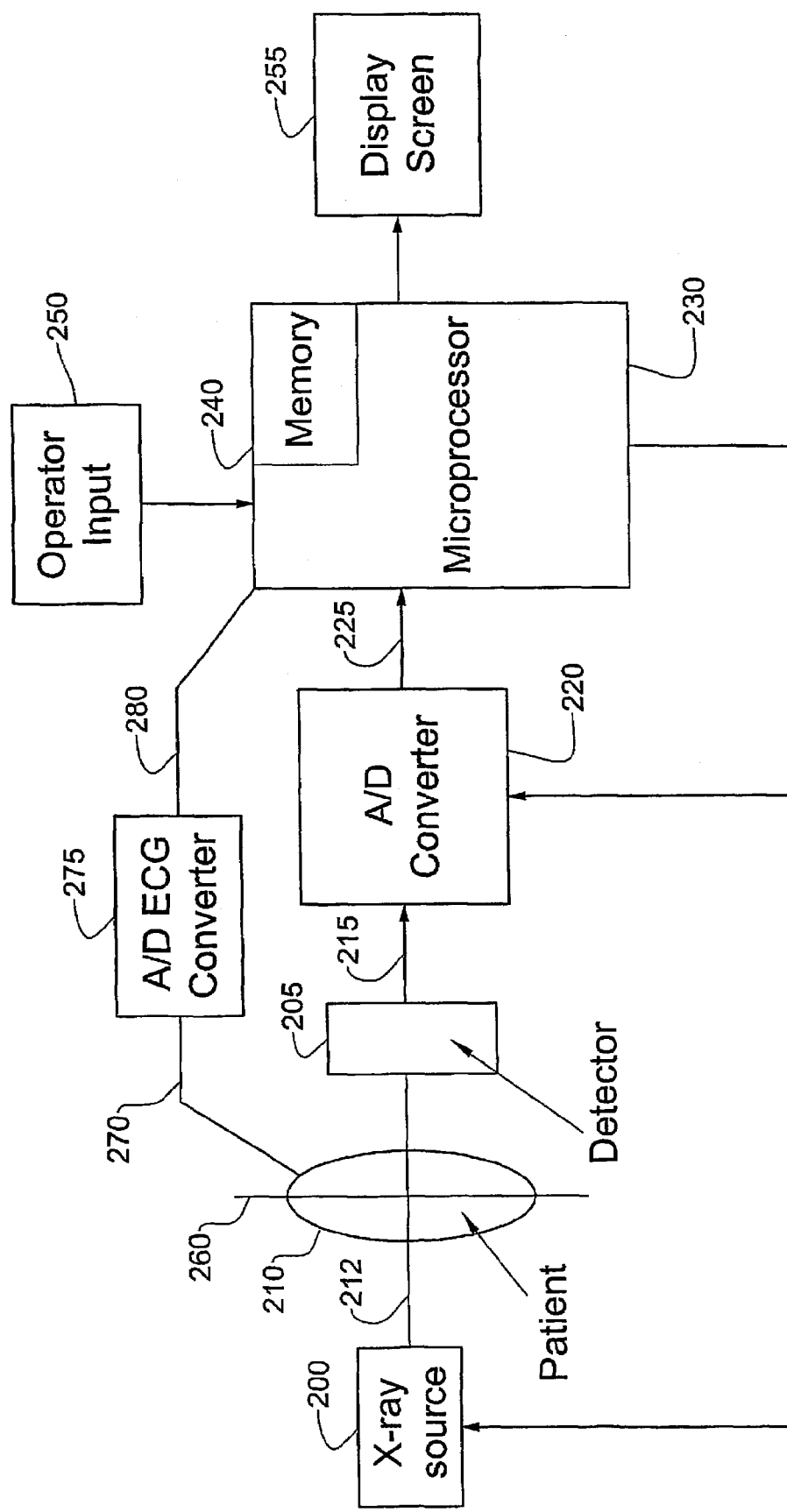
FIG. 2 is block diagram showing an embodiment of the system of the invention according to one embodiment of the invention.

In FIG. 2, a block diagram of a preferred embodiment of the system of the invention is shown. An X-ray source 200 and an X-ray detector 205 are used to obtain angiographic images of an individual 210. An X-ray beam 212 is produced by the X-ray source 200 and is detected by the detector 205 after having passed through the body of the individual 210. The analog signal 215 produced by the detector 205 is converted into a digital signal 225 by analog-to-digital converter 220. The digital signal 225 is inputted into a microprocessor 230 and stored in a memory 240. An analog ECG signal 270 may also be simultaneously obtained from the individual 210. The analog ECG signal 270 is converted into a digital signal 280 by analog-to-digital converter 275 and the digital ECG signal 280 is inputted to the microprocessor 230 and stored in the memory 240. The detector signal 225 and the ECG signal 280 are synchronized by the microprocessor 230. An operator input 250, that may be, for example, a key board or a computer mouse, is used to allow an operator to input instructions to the microprocessor 230. A display 255 is used to display images either in real-time or images called up from the memory 240.

The orientation of the X-ray beam 212 and the plane 260 of the individual's body may be selected by the operator in order to produce an image of an arterial tree of the individual, for example, the coronary artery tree, from a desired perspective. The operator inputs the desired perspective into the microprocessor 230 by means of operator input 250. The microprocessor 230 then brings the X-ray source 200 and the detector 205 into the required orientation by activating a mechanism (not shown) that moves the X-ray source and the detector into the desired orientation relative to the individual's body, as is known in the art.

The microprocessor 230 is programmed to generate a 3D reconstruction of the arterial tree based upon the obtained images. The 3D reconstruction of the arterial tree may be represented on display 255 using pseudo 3D effects such as directional lighting and shading. In a preferred embodiment, the reconstructed tree is presented as a stereoscopic pair of images on display 255 to be viewed by the operator using a stereoscopic viewer. The 3D reconstruction of the arterial tree may be manipulated on the display 255 by the operator by means of operator input 250, allowing him, for example, to zoom in on a specific region or to rotate the reconstruction on the display to obtain a desired perspective.

An artery of interest, for example, a stenotic artery, in an image or in the 3D reconstructed tree is selected by the operator or detected by the microprocessor, for example, by gray level analysis as is known in the art. For example, an image or the reconstructed tree may be displayed on the display 255, and an artery selected by the operator by means of input 250. The microprocessor determines from the 3D reconstruction of the arterial tree the angular orientation of the selected artery. The microprocessor then calculates two or more perspectives perpendicular to the axis of the selected artery. The perspectives preferably include two orthogonal perspectives. If images of the selected artery have not already been obtained approximately from the calculated perspectives, the operator obtains such images. The microprocessor 230 is programmed to reconstruct a 3D image of the selected artery based upon these images. The 3D reconstruction of the artery may be represented on display 255 using pseudo 3D effects such as directional lighting and shading. In a preferred embodiment, the reconstruction is presented as a stereoscopic pair of images on display 255 to be viewed by the operator using a stereoscopic viewer. The reconstruction of the artery may be presented to the operator embedded in the 3D reconstruction of the entire arterial tree.

The 3D reconstruction of the artery may be manipulated on the display 255 by the operator by means of operator input 250, allowing him, for example, to zoom in on a specific region or to rotate the reconstruction on the display to obtain a desired perspective, including an optimal perspective or a cross-section.

The microprocessor may optionally be programmed to determine quantitative and qualitative parameters of a stenosis based upon the 3D reconstruction. Such parameters may include, for example, the length and severity of a stenosis.

Figure 3:
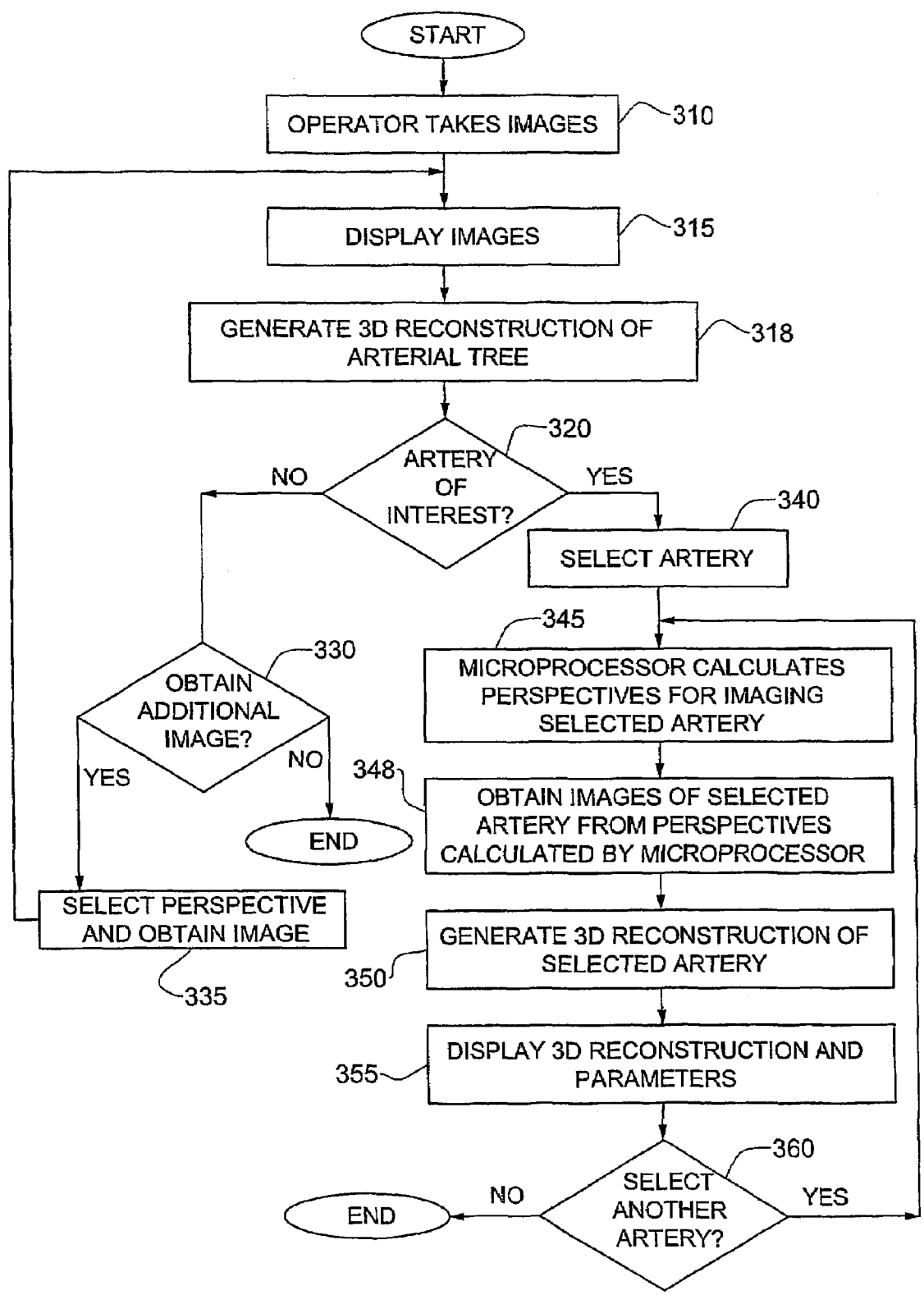
FIG. 3 is a flow chart diagram of the process of constructing a three-dimensional reconstruction of a stenotic artery.

Referring now to FIG. 3, a flow chart is shown describing a preferred embodiment of the process of the invention. At step 310 the operator obtains at least two angiographic images of an arterial tree of the individual 210 from different, preferably perpendicular, perspectives. The images are displayed on the display 255 in step 315, and a 3D reconstruction of the arterial tree is generated from the obtained images 318. The 3D reconstruction may optionally be displayed on the display 255. The obtained angiographic images or the 3D reconstructed tree is examined for arteries of interest, for example, stenotic arteries. The examination may be performed either automatically by the microprocessor 230 or by visual examination by the operator (step 320). If no artery of interest is detected in any of the images or in the 3D reconstructed tree the operator decides whether additional images are to be obtained from a new perspective (step 330). If at step 330 the operator decides not to obtain additional images, the process is terminated. If, at step 330 the operator decides to obtain an additional image, a perspective is selected and the operator inputs the perspective into the microprocessor 230, and the process then returns to step 315. If in step 320 one or more arteries of interest are observed, an artery of interest is selected in step 340. In step 345 the microprocessor calculates two or more perspectives perpendicular to the axis of the selected artery (step 348). The perspectives preferably include two orthogonal perspectives. If images of the selected artery have not already been obtained approximately from the calculated perspectives, the operator obtains such images (step 348). In step 350, the microprocessor updates the 3D reconstruction of the artery. The reconstructed artery is displayed on the display 255 in step 355 together with parameters describing the artery. For example, for a stenotic artery, the parameters may include the severity and length of the stenosis. The reconstructed artery may be presented to the operator embedded in the 3D reconstruction of the entire arterial tree. The operator may change the display using input 250, for example, by rotating the reconstructed artery on the display 255 so as to change the scale of the reconstruction of the artery or view the reconstruction from a desired perspective, including an optimal perspective or a cross-section. The operator then decides in step 360 whether he wishes to obtain a 3D reconstruction of another artery of interest in the arterial tree. If so, the process returns to step 340. If not, additional images are desired, the process terminates.

It will also be understood that the system according to the invention may be a suitably programmed computer. Likewise, the invention contemplates a computer program being readable by a computer for executing the method of the invention. The invention further contemplates a machine-readable memory tangibly embodying a program of instructions executable by the machine for executing the method of the invention.

In the method claims that follow, alphabetic characters used to designate claim steps are provided for convenience only and do not imply any particular order of performing the steps.

The invention claimed is:

1. A system for imaging an artery contained in an arterial tree, the artery having an axis, comprising:
   a a microprocessor configured to
   aa generate a three-dimensional reconstruction of the arterial tree from two or more angiographic images of the arterial tree obtained from different perspectives, wherein said images are produced by taking images after moving the angiographic source and detector into a required orientation defined by said different perspectives relative to a subject's body;
   ab determine an orientation of the axis of the artery in the arterial tree;
   ac calculate from the three-dimensional reconstruction of the arterial tree at least two perspectives of the artery perpendicular to the axis of the artery;
   ad obtain at least one angiographic image at each of the calculated perspectives from the previously obtained images if images were taken at the calculated perspectives, or by obtaining additional images that are produced by taking images after moving the angiographic source and detector into a required orientation defined by said calculated perspectives relative to the subject's body, if images taken at the calculated perspectives are not available from the previously obtained images; and
   ae generate a three dimensional reconstruction of the artery from angiographic images obtained essentially from the calculated perspectives.

2. The system of claim 1 wherein the microprocessor is further configured to display on a display any one or more of an angiographic image, the reconstruction of the arterial tree, or the reconstruction of the artery.

3. The system of claim 2 further comprising a display configured to display any one or more of an angiographic image, the reconstruction of the arterial tree, or the reconstruction of the artery.

4. The system according to claim 3 wherein the microprocessor is further configured to manipulate an image on the display.

5. The system of claim 3 wherein the microprocessor is configured to display on the display a view of the three-dimensional reconstruction of the arterial tree from a selected perspective.

6. The system of claim 3 wherein the microprocessor is configured to display on the display a view of the three-dimensional reconstruction of the artery from a selected perspective, such as a cross sectional perspective.

7. The system of claim 3 wherein the three-dimensional reconstruction of the artery is displayed on the display embedded in the three-dimensional display of the arterial tree.

8. The system of claim 1 wherein the microprocessor is further configured to make metrological measurements on the reconstruction of the arterial tree or the reconstruction of the artery.

9. A method for imaging an artery contained in an arterial tree, the artery having an axis, comprising:
   a generating a three-dimensional reconstruction of the arterial tree from two or more angiographic images of the arterial tree obtained from different perspectives wherein said images are produced by taking images after moving the angiographic source and detector into a required orientation defined by said different perspectives relative to a subject's body;
   b determining an orientation of the axis of the artery in the arterial tree;
   c calculating from the three-dimensional reconstruction of the arterial tree at least two perspectives of the artery perpendicular to the axis of the artery;
   d obtaining at least one angiographic image at each of the calculated perspectives from the previously obtained images if images were taken at the calculated perspectives, or by obtaining additional images that are produced by taking images after moving the angiographic source and detector into a required orientation defined by said calculated perspectives relative to the subject's body, if images taken at the calculated perspectives are not available from the previously obtained images; and
   e generating a three dimensional reconstruction of the artery from angiographic images obtained essentially from the calculated perspectives.

10. The method of claim 9 further comprising a step of displaying on a display any one or more of an angiographic image, the reconstruction of the arterial tree, or the reconstruction of the artery.

11. The method according to claim 10 further comprising a step of manipulating an image on the display.

12. The method of claim 10 further comprising a step of displaying a view of the three-dimensional reconstruction of the arterial tree from a selected perspective.

13. The method of claim 10 further comprising a step of displaying on the display a view of the three-dimensional reconstruction of the artery from a selected perspective, such as a cross sectional perspective.

14. The method of claim 13 wherein the three-dimensional reconstruction of the artery is displayed on the display embedded in the three-dimensional display of the arterial tree.

15. The method of claim 9 further comprising a step of making metrological measurements on the reconstruction of the arterial tree or the reconstruction of the artery.

16. The method according to claim 9 further including: e detecting in the three-dimensional reconstruction of the arterial tree a stenotic artery, the stenotic artery having an axis; and f analyzing the three-dimensional reconstruction of the artery for diagnosing stenosis in an arterial tree.

17. The method according to claim 16 wherein the step of analyzing the three-dimensional reconstruction of the artery includes determining the length or severity of the stenosis in the stenotic artery.

18. The method according to claim 17 wherein the stenotic artery has a lumen, the lumen has a cross-section of maximal narrowing, the cross-section of maximal narrowing has a fraction occluded by plaque, and determining the severity of the stenosis includes determining the fraction of the cross-section of maximal narrowing occluded by plaque.

19. The method according to claim 16 wherein the arterial tree is selected from the group comprising the coronary arterial tree, the renal arterial tree, the pulmonary arterial tree, the cerebral arterial tree, and the hepatic arterial tree.

20. A computer readable medium storing a computer program for performing all the steps of any one of claims 9 to 19 when said program is run on a computer.

* * * * *